United States Patent [19]

Sahm

[11] 4,052,433

[45] Oct. 4, 1977

[54] AROMATIC AZOMETHINES

[75] Inventor: Wilfried Sahm, Kelkheim, Taunus, Germany

[73] Assignee: Hoechst Aktiengesellschaft, Germany

[21] Appl. No.: 721,811

[22] Filed: Sept. 9, 1976

Related U.S. Application Data

[62] Division of Ser. No. 567,357, April 11, 1975, Pat. No. 3,994,879, which is a division of Ser. No. 427,016, Dec. 13, 1973, Pat. No. 3,892,807.

[30] Foreign Application Priority Data

Dec. 18, 1972 Switzerland ............... 18397/72

[51] Int. Cl.$^2$ ............................................. C07C 119/00
[52] U.S. Cl. .............................. 260/465 E; 260/519; 260/566 R; 260/566 F; 560/35
[58] Field of Search .......... 260/566 F, 566 R, 471 R, 260/465 E, 519

[56] References Cited

U.S. PATENT DOCUMENTS 3,864,390  2/1975  Le Count et al. .......... 260/566 F

OTHER PUBLICATIONS

Mathur et al., J. Chem. Soc. (London), 1960, pp. 1954–1955.

*Primary Examiner*—Gerald A. Schwartz
*Attorney, Agent, or Firm*—Connolly and Hutz

[57] ABSTRACT

Novel azomethines are obtained when reacting a tertiary amine with an aromatic aldehyde or ketone having in orthoposition an activated methoxy group. These azomethines are capable of ring closure to yield a benzofurane and said tertiary amine. The benzofuranes are optical brighteners, tranquilizers or intermediates for optical brighteners, fluorescent dyestuffs, scintillators, sensibilizers for electrophotographic coatings.

5 Claims, No Drawings

AROMATIC AZOMETHINES

This application is a division of application Ser. No. 567,357 filed Apr. 11, 1975, now U.S. Pat. No. 3,994,879, which is a division of application Ser. No. 427,016 filed Dec. 13, 1973 now U.S. Pat. No. 3,892,807.

The present invention relates to the preparation of furan compounds.

It has been proposed to prepare compounds of the general formula (1)

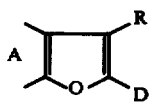
(1)

wherein A represents an aromatic mono- or polynuclear ring system which is condensed with the furan nucleus by two adjacent carbon atoms as indicated, R represents a hydrogen atom, an optionally substituted molecular alkyl group of 1 to 4 carbon atoms or an optionally substituted phenyl group and D represents an organic radical being conjugated with the furan radical, by splitting off water, using a strongly basic condensating agent, from a compound of the formula (2)

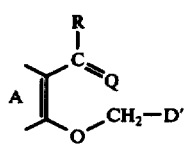
(2)

wherein A and R are defined as above and D' represents an organic radical which is conjugated with the double bonds of the furan nucleus after ring closure (U.S. pat. application Ser. No. 279.645)

The present invention provides a process for the preparation of compounds of the general formula (1), which comprises preparing compounds of the general formula (4)

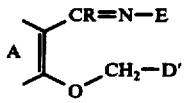
(4)

from compounds of the general formula (2) and from amines of the general formula (3)

E—NH$_2$ (3)

and splitting off an amine of the formula (3) from the compounds of formula (4) in the presence of strongly basic condensation agents in strongly polar solvents under ring closure.

In the formula (3) E stands for an aliphatic, aromatic carbo-or heterocyclic radical which is linked to the azomethine nitrogen atom via a tertiary carbon atom. In the formula (4) A, R and D' have the meanings given in the general formula (1) and (2).

The azomethines of the general formula (4) are prepared in a manner known per se at ambient or elevated temperature and, optionally, using solvents or diluents, for example, by heating them in toluene, chlorobenzene or other aromatic solvents, optionally in the presence of an acidic catalyst, such as a mineral acid or a strong organic acid, such as p-toluenesulfonic acid.

Suitable amines of the formula (3) are, for example aniline, α- and β-naphthylamine and the nucleus-substituted products of these aromatic amines or as an aliphatic amine the tertiary butyl amine. As these amines are split off during this reaction, the presence of substituents is, generally not advantageous in this case. However, for example amines of the general formula (3')

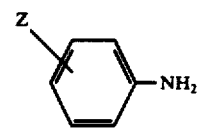
(3')

may carry substituents Z which do not hamper the reaction, for example halogen, especially chlorine atoms, alkyl or alkoxy group having 1 to 4 carbon atoms or hydroxyalkyl groups having 2 to 4 carbon atoms. Among the amines of the general formula (3) mentioned above, the anilines of the general formula (3') in which Z stands for a hydrogen atom or a chlorine atom, are preferred. Among these, especially the unsubstituted aniline is preferred (Z=H).

In the process of the invention, there are preferably prepared compounds of the formula (1')

(1')

by the intramolecular ringclosure of a compound of the general formula (4')

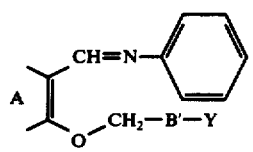
(4')

in strongly polar organic solvents under the action of strongly alkaline condensating agents.

The compounds of the general formula (4') are synthesized by reacting compounds of the general formula (2')

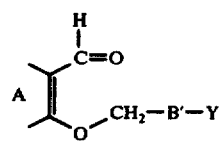
(2')

with aniline according to the process mentioned above.

In the general formulae (1') and (2') and (4'), A is defined as above. The other symbols are defined as follows:

B represents a direct bond or a continuously conjugated chain of carbon atoms, which is, wholly or in part, a constituent of a carbocylic or heterocylic ring system in which one or more than one carbon atoms may be replaced by hetero atoms, especially a nitrogen atom, and the double bonds are placed in such a manner that the molecule is completely conjugated;

B' is a direct bond or a continuously conjugated chain of carbon atoms which is, wholly or in part, a constituent of a carbocylic or heterocyclic ring system in which one or more than one carbon atoms may be replaced by hetrero atoms, especially by a nitrogen atom, and the double bonds are placed in such a manner that a molecule, which is completely conjugated, is formed after ring closure, Y represents an aryl, an optionally modified carboxy orsulpho group, an acyl, sulphonyl or nitro group, or if B' contains an aromatic ring, also a hydrogen atom.
One or more substituents Y may be bound to the carbo- or heterocyclic ring systems of B and B', but also further halogen atoms, especially chlorine atoms. Alkyl and/or alkoxy groups, especially lower alkyl and/or alkoxy groups may also be linked to B', and accordingly to B, but only if B' possesses electron-accepting groups, the electron-accepting influence of which on the $CH_2$—group overcompensates the effect of the said groups as electron-donors.

Suitable substituents which may be linked to A are of course only those which do not hamper nor heavily disturb the reaction. Halogen atoms, alkyl, alkylene, aryl and alkoxy groups are preferred. But, alkenyl, alkinyl, aralkyl, aralkenyl, aralkinyl, optionally modified carboxy or sulfo groups, aryl, and sulfonyl groups may also be linked to A. Suitable substitutents are especially those which contain aliphatic radicals having 1 to 4 carbon atoms and as aryl radical a phenyl radical. All substituents are not allowed to carry hydrogen atoms which can be replaced by metal atoms in a more easy or similarly easy manner as compared with the hydrogen atoms of the $CH_2$—group in the formulae (4), (4') or the following formula (4").

Functionally modified carboxy groups are, firstly, their salts with colourless cations, alkali metal ions or ammonium ions being preferred. There may, furthermore, be mentioned, the cyano group (nitrile group), the carboxylate group or the carboxylic acid amide group. Carboxylate groups are especially those of the general formula $COOR^1$, wherein $R^1$ is a phenyl radical or a lower alkyl group optionally having a branched chain, which radicals may contain further substituents, for example, a preferably low-molecular dialkylamine, lower trialkylammonium or alkoxy group in which dialkylamino or trialkylammonium groups two alkyl groups may be replaced by a ring, such as is in the morpholino or piperidino groups. A carboxylic acid amide group is especially one of the formula $CONR^2R^3$ wherein the radicals $R^2$ and $R^3$ each represents a hydrogen atom or a lower alkyl group which may be, optionally, substituted, which may also form together with the nitrogen atom a hydroaromatic ring, which optionally, may carry furtherhetero atoms, such as oxygen or nitrogen atoms, for example, a piperidino or morpholino group.

Functionally modified sulpho groups are, by analogy with the description given above, the salts with colourless cations, preferably alkali metal ions or ammonium ions, and derivatives in which the $SO_2$-group is linked to a hetero atom, as to be found in the sulphonate group and in the sulphonamide group. A sulphonate group is especially one of the formula $SO_2OR^1$ wherein $R^1$ is defined as above and a sulphonamide group is one of the formula $SO_2NR^2R^3$ wherein $R^2$ and $R^3$ are defined as above.

An acyl group is especially one of the formula $COR^4$ wherein $R^4$ is preferably lower alkyl or a phenyl radical which may optionally be substituted.

A sulphonyl radical is especially one of the formula $SO^2R^5$ wherein $R^5$ represents a lower alkyl or a phenyl radical, optionally substituted, each of which may carry as substituents preferably a lower dialkylamino, lower trialkyl ammonium, acylamino (each as defined above) or sulpho group.

The present invention also provides a process for preparing a compound of the general formula (1")

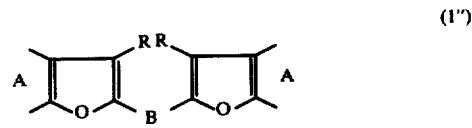

which comprises splitting off amine from compounds of the general formula (4")

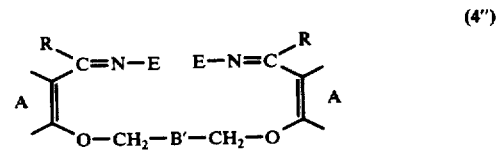

i.e. the radical D or D' contains itself a furan radical or its precursor.

The radicals A, B, B', E and R of these formulae have the same definitions as given above.

The preparation of compounds of the general formula (4") (E = preferably phenyl and B' = preferably p,p'-diphenyl) is carried out in a manner analogous to the preparation of the compounds of the general formulae (3) and (3'), for example from the corresponding dialdehydes or diketones (2")

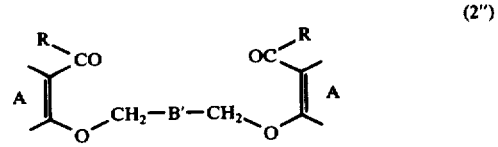

The precusors (2), (2') and (2") are reaction products of compounds of the general formulae (5)

in which M represents an alkali metal or an alkaline earth metal cation and A and R are as defined in the general formula (1), with compounds of the general formula (6). (6') or (6")

in each of which X represents a radical which can easily be split off as anion, preferably the anion of an inorganic acid, preferably of a hydrohalic acid and D', B', and Y are as defined in the general formula (2) and (2'), in an organic solvent.

The alkali metal or alkaline earth metal salts (5) may, for example, be the following:

Salicylic aldehyde, 5-chloro-salicylic aldehyde, 3,5-dichloro-salicylic aldehyde, 3-bromosalicylic aldehyde, 4-bromo-salicylic aldehyde, 5-bromosalicylic aldehyde, 3,5-dibromosalicylic aldehyde, 3-fluoro-salicylic aldehyde, 3-chloro-salicylic aldehyde, 6-methyl-salicylic aldehyde, 5-chloro-6-methylalicylic aldehyde, 3-methyl-salicylic aldehyde, 5-methylsalicylic aldehyde, 4-methyl-salicylic aldehyde, 5-chloro-4-methyl-salicylic aldehyde, 6-ethyl-salicylic aldehyde, 4-ethyl-salicylic aldehyde, 3,5-dimethyl-salicylic aldehyde, 4,5-dimethyl-salicylic aldehyde, 3-phenyl-salicylic aldehyde or 5-phenyl-salicylic aldehyde, 2-hydroxy-acetophenone,2-hydroxy-4-chloro-acetophenone, 2-hydroxy-benzophenone, 2-hydroxy-4,5-dimethyl-acetophenone or 2-hydroxy-(α-methoxy)-acetophenone.

As compounds of the general formula (6), (6') and (6") there may be mentioned, for example, the following substances: benzylchloride, p-cyano-benzylchloride, p-carbomethoxy-benzylchloride, p-nitro-benzylchlorine, p-trifluoromethyl-benzlchloride, o-trifluoromethyl-benzyl-chloride, 2,3,4,5,6-pentafluoro benzylchloride, m-trifluoromethyl benzylchloride, 4-bromomethyl benzosulphonic acid-dimethylamide, 2-chloromethyl-4-nitrophenol, 4-chloromethyl-α-phenyl-anisol, 5-bromo-ethyl-3-(4-tolyl)-1,2,4-oxadiazole, 5-bromo-pentadiene-(1,3), 1-cyano-5-chloro-pentadiene-(1,3), cinnamyl chloride, cinnamyl bromide, 1,1-diphenyl-2-bromo methyl-ethylene, 2-bromoethyl-benzofuran, 3-bromo-ethyl-benzofuran, 3-bromomethyl-thiophene, 4,4'-bis-chloromethyl -diphenyl, 4,4'-bischloromethyl-diphenyl ether, 2-bromomethyl-4,5-benzo-benzofuran, 2-chloromethyl-benzoxazole, 5-chloro-1-(2'-benzoxazoly)-pentadiene-(1,3), 2-chloromethyl-4,5-benzo-benzoxazole, 2-chloromethyl-5,6-benzo-benzoxazole, 2-chloromethyl-6,7-benzo-benzoxazole, 2-chloro-methyl-5-methyl-benzoxazole, 2-chloromethyl-5,6-dimethyl-benzoxazole, 2-bromomethyl-5-carbomethyoxy-furan, 2-bromo-methyl-5-cyanofuran, 2-bromomethyl-5-carbomethoxy-thiophene, 2-bromomethyl-5cyano-thiphene, 2-chloromethyl-pyridine, 3-chloromethyl-pyridine, 4-chloromethyl-pyridine, 2-chloromethyl-quinoline, 1-bromo-methyl-4-cyano-naphthalene, 1-bromomethyl-4-carbomethoxy-naphthalene and chloroacetonitrile.

Intermediate of the formula (4) which can be prepared according to the invention are, for example, the following:

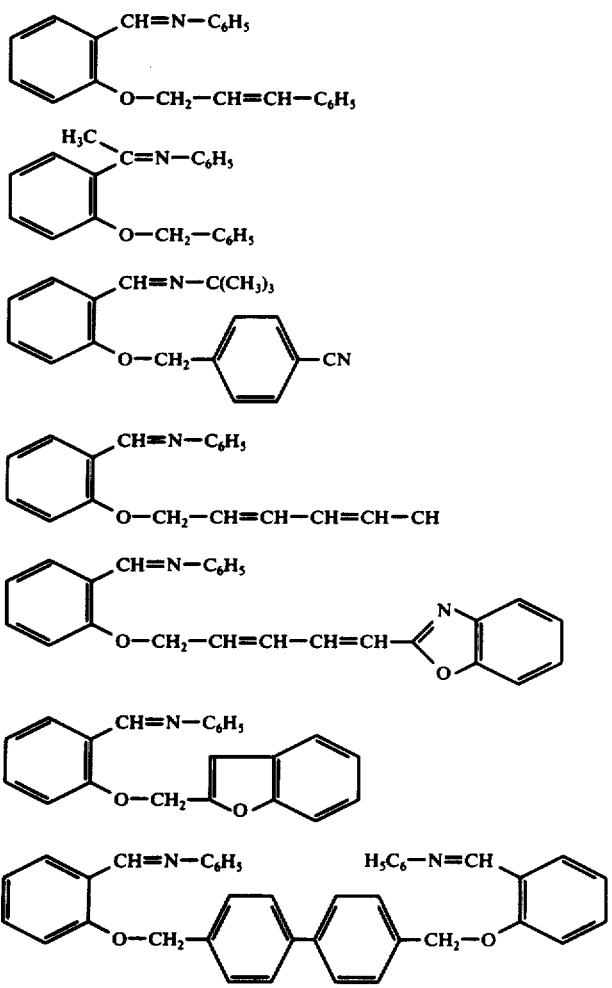

The ring closure reaction of the invention is carried out in strongly polar, neutral to alkaline organic solvents which are free form atoms capable of being replaced by alkali metals, especially hydrogen atoms. There may be used, for example, as solvents alkylated acyl amides of the general formula (8)

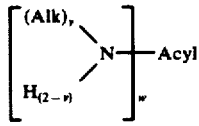

(7)

wherein "Alk" is a lower alkyl group having not more than 4 carbon atoms, "Acyl" is the radical of a low-molecular carboxylic acid having not more than 4 carbon atoms, especially formic acid and acetic acid, or the phosphoric acid radical, $w$ indicates the basicity of the acid, i.e., how many base equivalents the acid can bind, and $v$ is zero or the numbers 1 or 2, preferably 1 or 2, especially 2.

The following solvents may, for example, also suitably be used: tetramethyl urea, N-methyl-pyrrolidone, acetonitrile or pyridine.

The solvents, however which are of the general formula (7) are espcially important, among which those are preferred in which $v$ is 2. Dimethyl formamide, hexamethyl-phosphoric acid trisamide, diethyl-formamide and dimethyl-acetamide are of special interest.

The solvents can be used separately or in admixture with one another.

For the condensation reaction, strongly basic condensation agents are required, which are, for example, the strongly basic alkaline earth metals and especially alkali metal compounds, for example, the hydroxides, amides, hydrides, sulphides, alcoholates and strongly basic ion exchangers thereof, and further aluminum hydride, nitride or alcoholates.

The alcoholates to be used are especially derived from linear-chain, branched-chain or cyclic lower aliphatic alcohols having up to 8 carbon atoms, preferably from linear-chain alkanols having from 1 to 4 carbon atoms.

The sodium or potassium compounds are preferably used, the hydroxides, amides and alcoholates thereof are of special interest in practice. Mixture thereof may, of course, also be used.

The alkaline condensation agents are preferably used in at least the equivalent amount, but also, if necessary, a many times equivalent amount may be used especially if the compounds to be condensated contain groups capable of being hydrolized or if higher temperatures are required in which case part of the condensation agent may be consumed by reaction with the solvent.

When the starting compounds to be condensated contain radicals sensitive to hydrolysis, for example, carboxylic acid ester groups, condensation products are isolated, especially at high reaction temperatures, in which these groups are present in hydrolysed state, for example, the free carboxylic acids or the corresponding salts thereof, depending on the method of working up.

The process of the invention has the special advantage that working is usually possible at smooth reaction conditions. Reaction temperatures above 150° C are not necessary, temperatures above 120° C are only required in exceptional cases.

Frequently, the reaction is carried out at room temperature without external heating, which especially occurs when using potassium alcoholates or potassium hydroxide. In some cases it is advantageous or even necessary to heat the reaction mixture which is advantageously covered by nitrogen, slowly to 30° - 120° C and to maintain that temperature for a certain time.

The essential advantage of the process of the invention is that its reaction can easily be carried out and that almost quantitative yields are obtained especially also in those cases in which the formation of carbanions is not especially activated, for example in the case of compounds of the general formula (4").

The reaction product can be isolated from the reaction mixture according to usual methods known per se.

The compounds of the general formula (1) which can be prepared by the reaction described above are optical brighteners or- if nitro groups are present - precursors of brighteners which may be transformed to brighteners by reduction of the nitro group to the amino group, e.g. by catalytic hydrogenation. They are also valuable intermediate products for a variety of syntheses, for example, for the preparation of dyestuffs, scintillators and pharmaceutical products and for electrophotographic coatings. Optical brighteners of this type are known, for example, from German Offenlegungsschriften Nos. 2,031,774 and 2,105,305, pharmaceutical products, for example, from U.S. Pat. No. 3,470,192.

The following examples illustrate the invention:

EXAMPLE 1

21.1 g of ω,ω'-bis-(o-formyl-phenoxy)-dibenzyl were heated to the boil with 4.7 g of aniline and 0.05 g of p-toluene-sulfonic acid in 250 ml of toluene for 2 hours and the water was separated via a water separator. The mixture was then allowed to cool, the precipitate which had formed, was suction-filtered, washed with methanol and dried at 60° C in vacuo. 27.1 of the compound (101) of the formula (101)

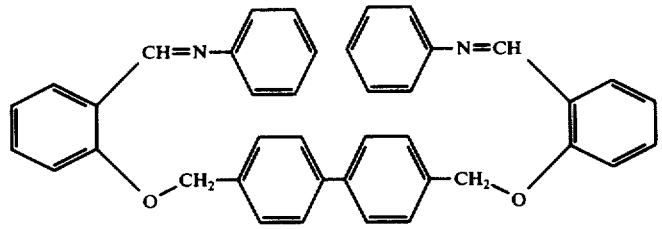

were obtained having a melting point of 220°-222° C (after-recrystallization from dimethylformamide).

In manner analogous to that of compound (101), the azomethines characterized in the following table 1 may be synthesized.

Table 1

| No. in sequence | Constitution | Melting point °C | Solvent |
|---|---|---|---|
| (102) | | 195–197 | DMF |
| (103) | | 168–165 | DMF |
| (104) | | 172.5 | DMF |
| (105) | | 185–189 | DMF |
| (106) | | 176–180 | DMF |
| (107) | | resinic, not crystalline | |

| No. in sequence | Constitution | Melting point °C | Solvent |
|---|---|---|---|
| (108) | (structure: 2-(benzyloxy)phenyl methyl ketone N-phenylimine; CH₃–C(=N–C₆H₅)– attached to phenyl with o-OCH₂–C₆H₅) | fair yellow oil | |
| (109) | (structure: 2-[(4-cyanobenzyl)oxy]benzaldehyde N-phenylimine; CH=N–C₆H₅; o-O-CH₂-C₆H₄-C≡N) | 79–81 | from n-butanol |
| (110) | (structure: 2-(cinnamyloxy)benzaldehyde N-phenylimine; CH=N–C₆H₅; o-O-CH₂-CH=CH-C₆H₅) | 125–125.5 | from n-butanol |
| (111) | (structure: CH=N–C₆H₅; o-O-CH₂-(4-benzofuran-2-yl-phenyl)) | 132–134 | crude product |
| (112) | (structure: naphthalene with CH=N–C₆H₅ and O-CH₂-benzofuran-2-yl) | 87–95 | (crude product) |
| (112a) | [ CH=N–C₆H₄–Cl ; o-O-CH₂-C₆H₄– ]₂ | 167–169 | |

Table 1-continued

| No. in sequence | Constitution | Melting point °C | Solvent |
|---|---|---|---|
| (112b) | [structure: CH=N-(2-Cl-phenyl), with benzene-O-CH₂-phenyl, bracketed ×2] | 160–163 | |
| (112c) | [structure: CH=N-(3-Cl-phenyl), with benzene-O-CH₂-phenyl, bracketed ×2] | 179–181 | |

An isolation of the intermediate or purification of the azomethines is generally, however, not necessary. Preferably, the solvents used for the preparation of the azomethines are distilled off in vacuo, then replaced by a suitable dipolar solvent and the ring closure reactions described in Example 2 to 6 are immediately carried out.

EXAMPLE 2

31.4 g of the compound (109) were dissolved at room temperature in 250 ml of dimethylformamide, 6 g of potassium hydroxide (pulverized, about 95%) were added and the mixture was stirred for 45 minutes without external heating. Then, the reaction mixture was stirred into 500 ml of ice water and the mixture was neutralized with 2 N HCL. The mixture was suction-filtered, the filter residue washed with water and dried at 60° C in vacuo. 21.5 g of the crude product of the formula (113)

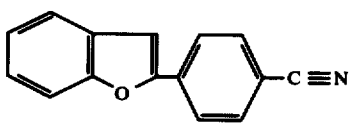
(113)

were obtained which had a melting point of 137°–139° C.

The compound was purified by recrystallization from gasoline (melting range: 100°–150° C) and then had a melting point of 141.5°–142.5° C.

EXAMPLE 3

57.2 g of the compound (101) were suspended in 400 ml of dimethyl formamide, 12.55g of potassium hydroxide (pulverized, about 90%) were added and the reaction mixture was slowly heated to 100°–120° C. This temperature was maintained for 3 hours. Then the batch was allowed to cool to room temperature and the precipitate which had formed, was suctionfiltered. The filter residue was washed with dimethyl formamide, then with water until it became neutral and then dried at 60° C in vacuo. 36 g of crude product of the formula (114)

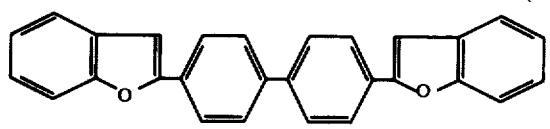
(114)

were obtained which could be purified by recrystallization from α-chloronaphthalene.

Melting point: > 350° C. $C_{28}H_{18}O_2$ Calculated: C 87.9, H 4.79. (386.45) Found: 87.7, H 4.80. λmax. (absorption/DMF): 351 nm, ε = 7.06 . 10⁴.

EXAMPLE 4

36.3 g of the compound (110) were dissolved in 400 ml of N,N-dimethylacetamide, 12.2 g of potassium tertiary butylate were added and the mixture was heated to 80°–90° C for 2 hours while stirring. After cooling, it was worked up as described in example 2. 26 g of crude product of the formula (115)

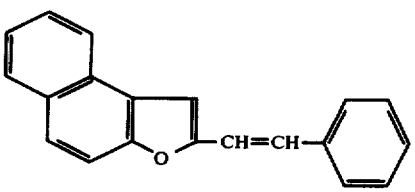
(115)

were obtained which could be purified by recrystallization from n-butanol while adding active charcoal. Melting point: 176°–177° C.

EXAMPLE 5

40.3 g of the compound (111) were dissolved in 400 ml of dimethyl formamide, 7 g of potassium hydroxide (pulverized, about 85%) were added, the mixture was stirred at 60° C for 30 minutes, then at 115° C for 60 minutes. It was cooled in the ice bath to about 5° C and the pecipitate which had formed, was suction-filtered. It was first washed with methanol, then with water. After drying at 60° C in vacuo, 30.5 g of the crude product of the formula (116)

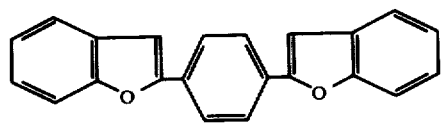
(116)

were obtained, which were recrystallized from dimethyl formamide with the addition of active charcoal.
Melting point: 308°–309° C

EXAMPLE 6

37.7 g of the compound (112) were dissolved in 400 ml of hexamethyl-phosphoric acid trisamide and 7 g of sodium hydroxide were added. The mixture was stirred at 60° C for 2 hours and working up followed as described in example 2. So, 25 g of crude product of the formula (117)

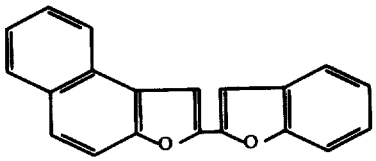
(117)

were obtained which had a melting point of 171° C.

In a manner analogous to that described in the preceding examples the compounds listed in the following table, were prepared.

TABLE 2

| No. in sequence | Constitution | Melting point °C | Solvent | alkali metal compound | reaction temperature °C |
|---|---|---|---|---|---|
| 118 | (naphthofuran-phenyl-C≡N) | 173–175 | DEF | NaOH | 40 |
| 119 | (naphthofuran-phenyl-NO₂) | 218–220 | DMF | KOH | 25 |
| 120 | (benzofuran-CH=CH-phenyl) | 124–125 | DMF | KOH | 100 |
| 121 | (naphthofuran-phenyl-COOCH₃) | 199–200 | HMPT | KOH | 25 |
| 122 | (benzofuran-naphthyl-C≡N) | 126–128 | DMA | KOH | 25 |

TABLE 2-continued

| No. in sequence | Constitution | Melting point °C | Solvent * | alkali metal compound | reaction temperature °C |
| --- | --- | --- | --- | --- | --- |
| 123 | benzofuran-naphthalene-COOCH₃ | 114.5 | DMF | KO-tert.-butylate | 25 |
| 124 | 3-methyl-2-phenylbenzofuran | 35–36 | DMF | KO-tert.-butylate | 120 |
| 125 | benzofuran-naphthalene-COOH | 222–223 | DMF | NaOH | 90 |
| 126 | 5-methylbenzofuran-naphthalene-CN | 195 | DMF | NaOH | 25 |
| 127 | 5-tert-butylbenzofuran-naphthalene-CN | 140 | DMF | KOH | 25 |
| 128 | 2,2'-bibenzofuran | 197–198 | DMF | KOH | 100 |
| 129 | 1,4-bis(3-methylbenzofuran-2-yl)benzene | 145 | DMF | KOH | 110 |
| 130 | benzofuran-phenyl-CH=CH-benzofuran | 290 | DMF | KOH | 110 |
| 131 | benzofuran-naphthoxazole | 204 | DMF | KOH | 90 |
| 132 | benzofuran-naphthoxazole isomer | 298 | DMF | KOH | 90 |

TABLE 2-continued

| No. in sequence | Constitution | Melting point °C | Solvent | alkali metal compound | reaction temperature °C |
|---|---|---|---|---|---|
| 133 | | 171–172.5 | DMF | KOH | 90 |
| 134 | | 144–145.5 | DMF | NaOH | 90 |
| 135 | | 127–128 | DMF | NaOH | 90 |
| 136 | | 170–172 | DMF | KOH | 90 |
| 137 | | 193–194 | DMF | KOH | 90 |
| 138 | | >350 | DMA | NaOH | 125 |
| 139 | | >350 | DMA | NaOH | 125 |
| 140 | | >350 | DMA | NaOH | 125 |
| 141 | | >350 | HMPT | KO-tert.-butylate | 125 |
| 142 | | >350 | DMA | KOH | 120 |

TABLE 2-continued

| No. in sequence | Constitution | Melting point °C | Solvent | alkali metal compound | reaction temperature °C |
|---|---|---|---|---|---|
| 143 | | >350 | DMF | KOH | 120 |
| 144 | | 121 | HMPT | KOH | 80 |

*DMF = dimethyl formamide
DEF = diethyl formamide
DMA = dimethyl acetamide
HMPT = hexamethyl-phosphoric acid trisamide.

I claim:
1. A compound of the formula

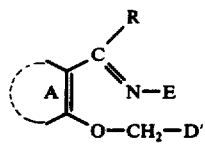

in which A is phenyl or naphthyl which is unsubstituted or substituted by halogen, lower alkyl, lower alkoxy, lower alkylene forming an annellated ring, or phenyl, R is hydrogen, lower alkyl or phenyl, E is lower tertiary alkyl, phenyl, chlorophenyl, lower alkyl phenyl, lower hydroxyalkyl phenyl or naphthyl and D' is phenyl, naphthyl, styryl, or a bivalent group selected from ethenylene, phenylene and p,ω-styrylene which bivalent group is substituted by a group of the formula

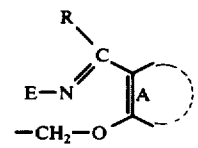

in which A, R and E are as defined above, which radical D' may be substituted by carboxy, lower carboalkoxy, cyano, or nitro.

2. A compound as defined in claim 1, wherein A is phenyl, mono- or di-(lower alkyl)-phenyl, indanyl, tetrahydronaphthyl or naphthyl; R is hydrogen or methyl; E is phenyl or chlorophenyl and D' is phenyl, cyanophenyl, carboxyphenyl, lower carboalkoxyphenyl, or nitrophenyl; naphthyl, cyanonaphthyl, carboxynaphthyl, lower carboalkoxynaphthyl; styryl, or a bivalent group selected from ethenylene, phenylene and p,ω-styrylene which bivalent group is substituted by a group of the formula in which A, R and E are as defined above.

3. A compound as defined in claim 1, wherein A is phenyl, tolyl, xylyl, tert.-butyl phenyl, indanyl or naphthyl, R is hydrogen or methyl, E is phenyl or chlorophenyl and D' is phenyl, cyanophenyl or styryl

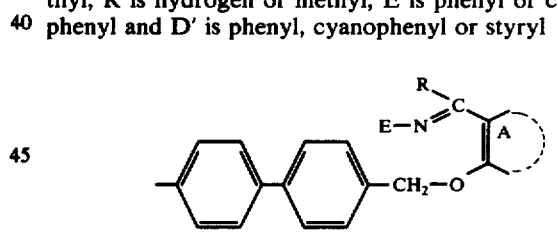

4. A compound as defined in claim 1, wherein R is hydrogen and E is phenyl.

5. The compound as defined in claim 1, wherein A is phenyl, R is hydrogen, E is phenyl and D' is p-cyanophenyl.

* * * * *